US00PP07857P

United States Patent [19]

Ishizawa

[11] Patent Number: Plant 7,857

[45] Date of Patent: Apr. 21, 1992

[54] APPLE TREE BENI TSUGARU

[75] Inventor: Kunihiko Ishizawa, Aomori, Japan

[73] Assignee: Nakajima Tenkoen Co., Ltd., Higashine, Japan

[21] Appl. No.: 483,855

[22] Filed: Feb. 23, 1990

[51] Int. Cl.[5] ..... A01H 5/00
[52] U.S. Cl. ..... Plt./34
[58] Field of Search ..... Plt. 34

*Primary Examiner*—James R. Feyrer

*Attorney, Agent, or Firm*—Armstrong, Nikaido, Marmelstein, Kubovcik & Murray

[57] ABSTRACT

An apple tree characterized by medium vigor and spreading tendency, producing a fruit which colors solid red earlier than the known "Tsugaru" variety. The fruit has an oblong shape, without crowning. The flesh of the fruit is creamy white, very juicy, lightly flavored, and moderately sweet with low acidity and very little browning.

13 Drawing Sheets

BACKGROUND OF THE INVENTION

This invention involves a spontaneous color sport of the popular Japanese apple variety "Tsugaru", a fall ripening variety of apple which is normally characterized by having skin coloration with red stripes over a yellow-green ground color at maturity. The new and distinct apple variety is earlier coloring and a more solid red color at maturity. It is anticipated that this color sport will be more attractive to most segments of the consuming public from the standpoint of eye appeal, as compared to its parent "Tsugaru". The new variety has been named "Beni Tsugaru". The genus and species of the new variety is *Malus pumila* Mill.

The new variety of apple tree has been repeatedly asexually reproduced by placing buds of "Beni Tsugaru" on mature trees of other varieties. Such asexual reproductions have run true to the original discovery in every distinguishing respect by producing the earlier coloring and more highly colored fruit described herein, to establish that the variety is stable.

SUMMARY OF THE VARIETY

The apple tree variety of this invention, "Beni Tsugaru", is a bud mutation of the known "Tsugaru" apple tree variety. "Beni Tsugaru" in general is similar to "Tsugaru" with respect to trunk, branch, leaves and flowers, but is distinguished from "Tsugaru" because it developes fruit color with indistinct stripes about 20 days earlier than "Tsugaru".

Each of FIGS. 5–8 is a photograph of "Beni Tsugaru" apples (right) compared to "Tsugaru" apples.

Figure 1:
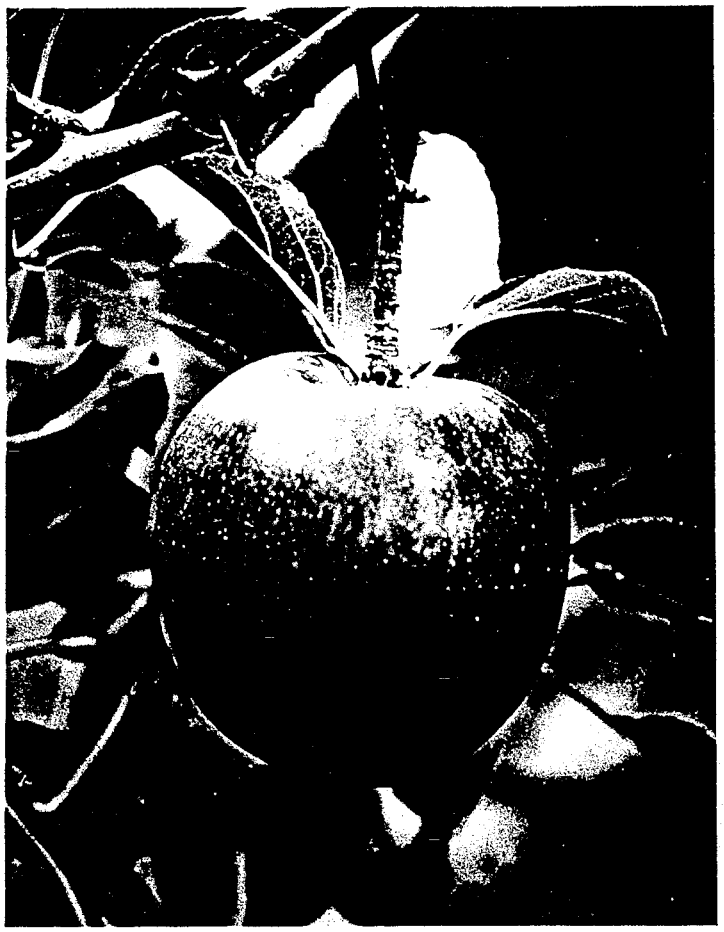
FIG. 1 is a photograph of a "Beni Tsugaru" apple on the original limb.
Figure 2:
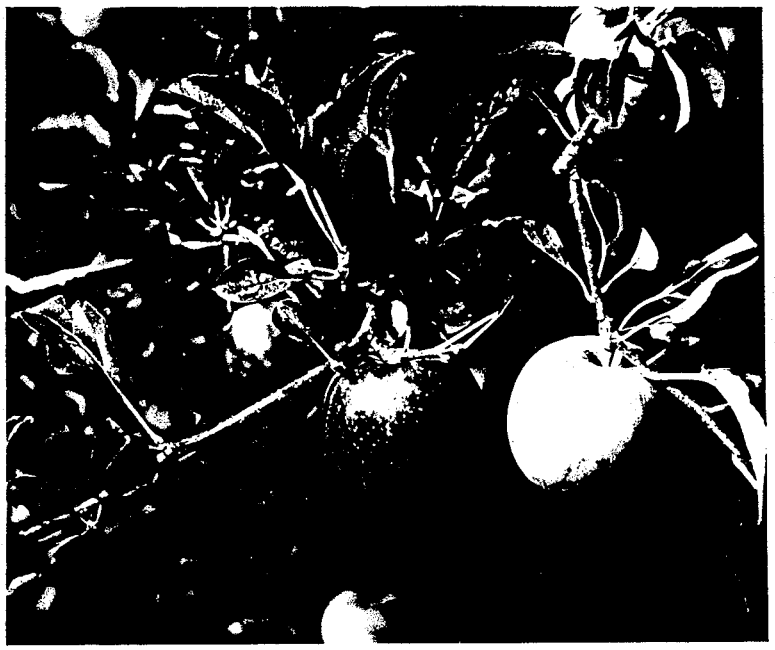
FIG. 2 is a photograph of a "Beni Tsugaru" apple compared with a "Tsugaru" apple (green fruit at the back).
Figure 3:
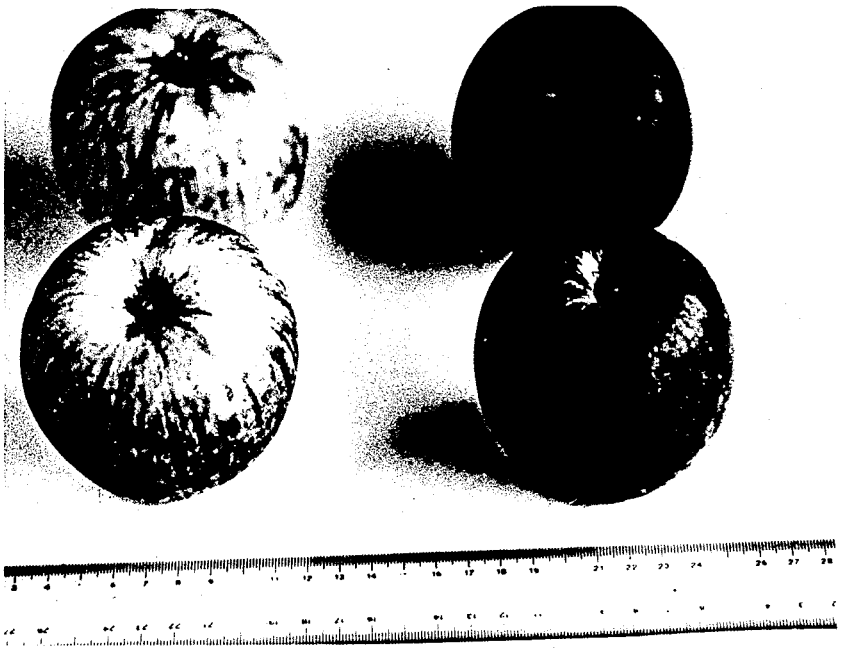
FIG. 3 is a photograph of a "Beni Tsugaru" apple (left) compared to a "Tsugaru" apple (right).
Figure 4:
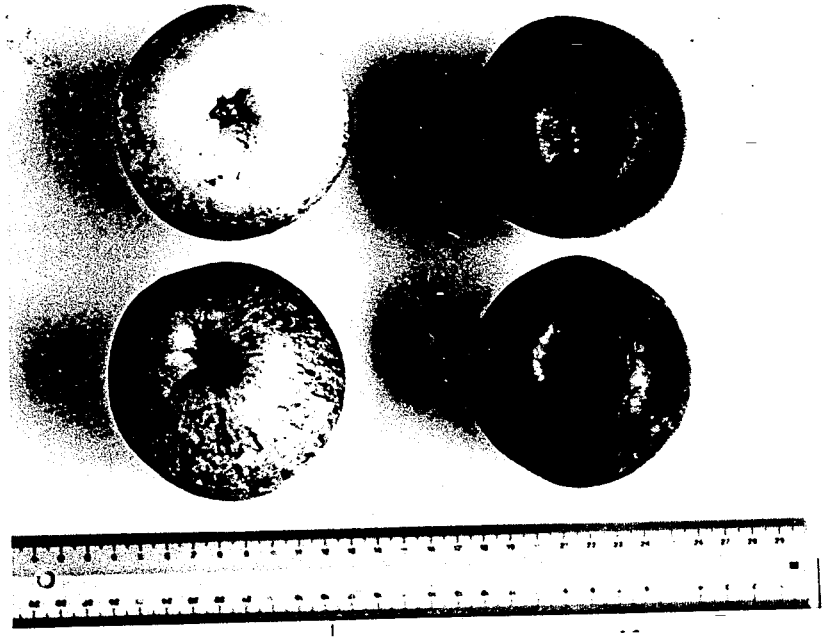
FIG. 4 is a photograph of the original limb of "Beni Tsugaru". (Red fruit is "Beni Tsugaru", green fruit is "Tsugaru".)
Figure 5:
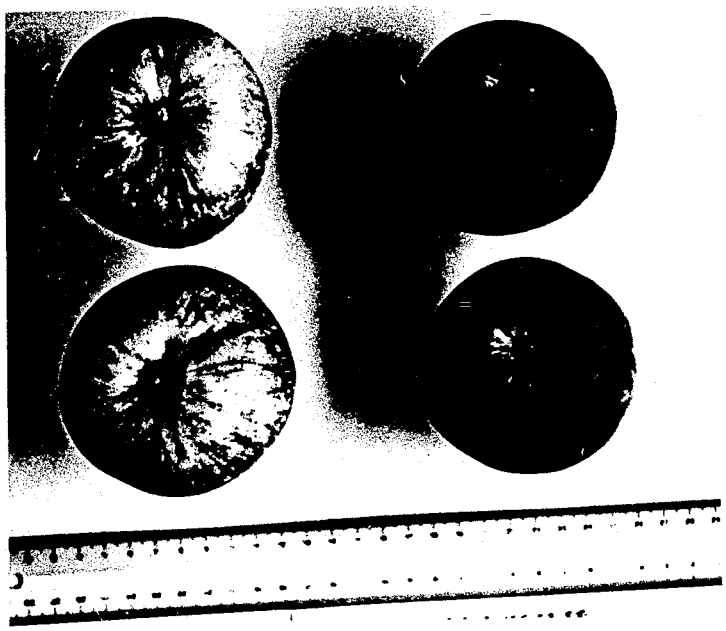
Figure 6:
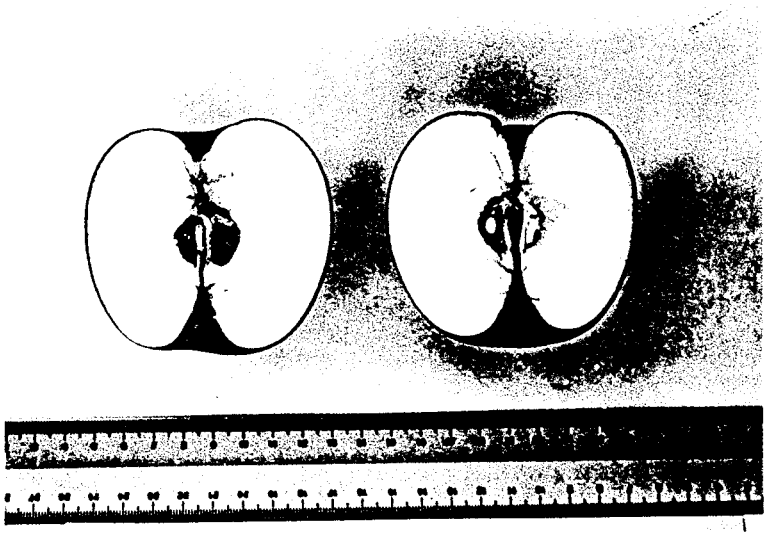
Figure 7:
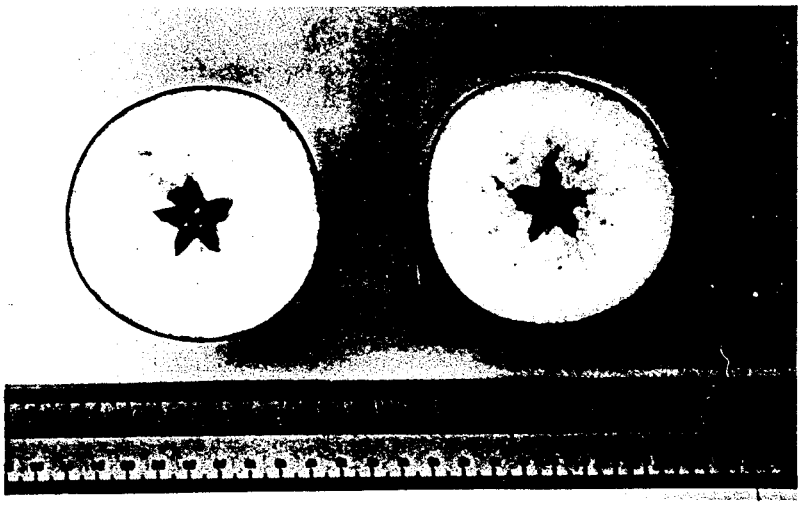
Figure 8:
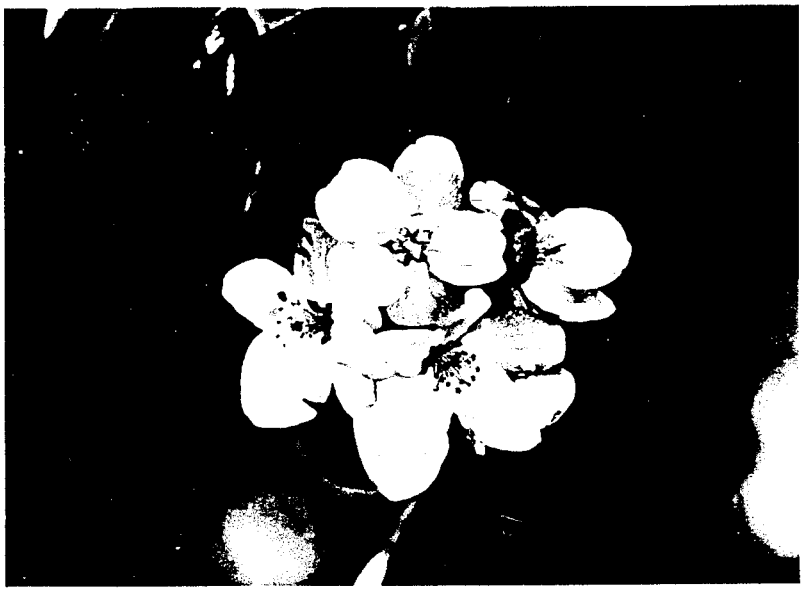
Figure 9:
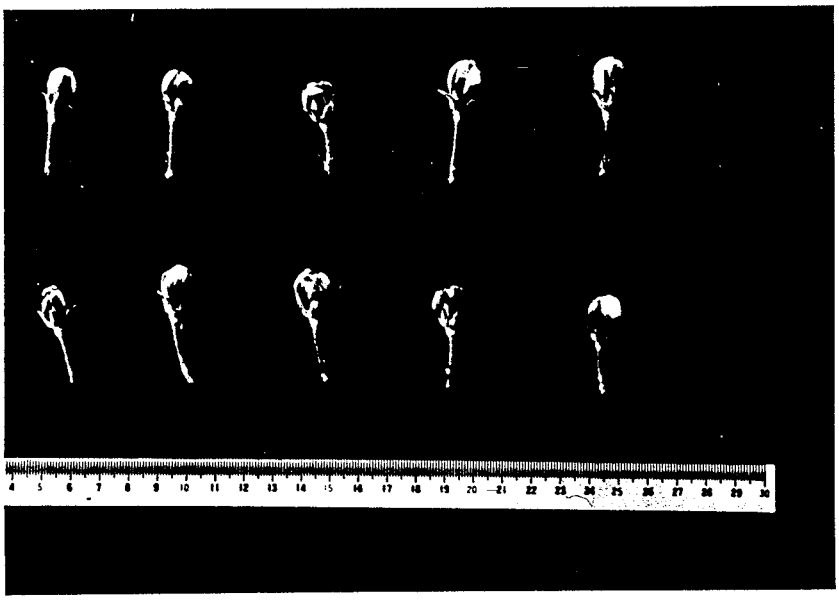

FIG. 9 is a photograph of a longitudinal section of a "Beni Tsugaru" apple.

Figure 10:
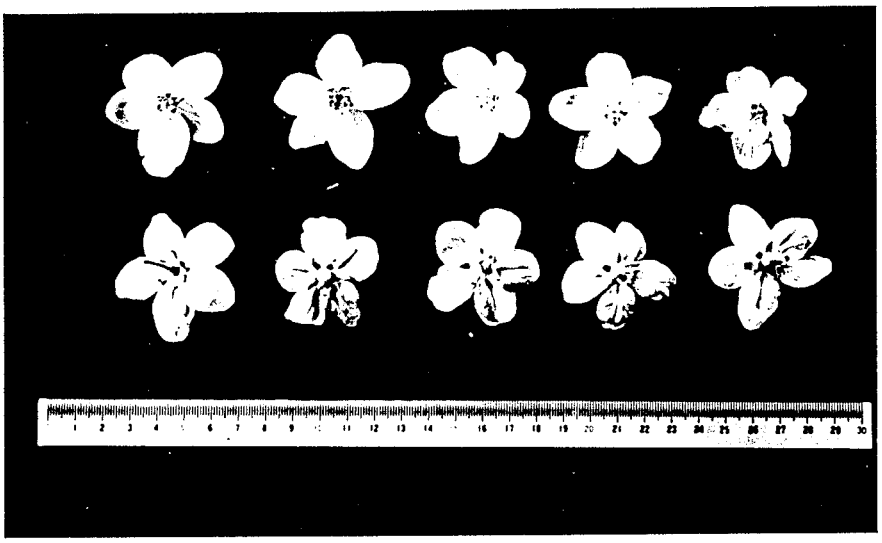

FIG. 10 is a photograph of a cross-section of a "Beni Tsugaru" apple.

Figure 11:
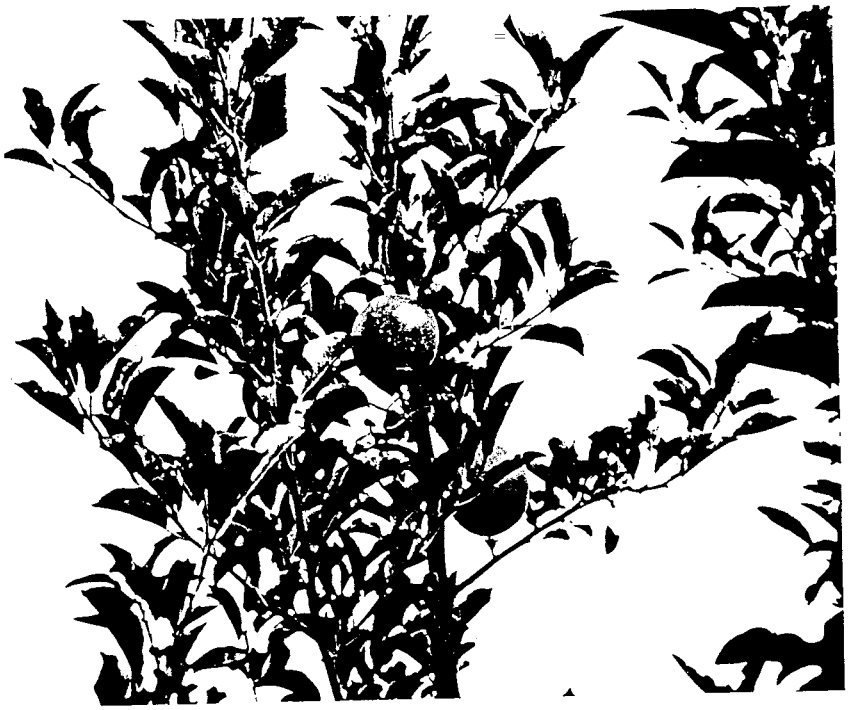

FIG. 11 is a photograph of seeds of a "Beni Tsugaru" apple.

Figure 12:
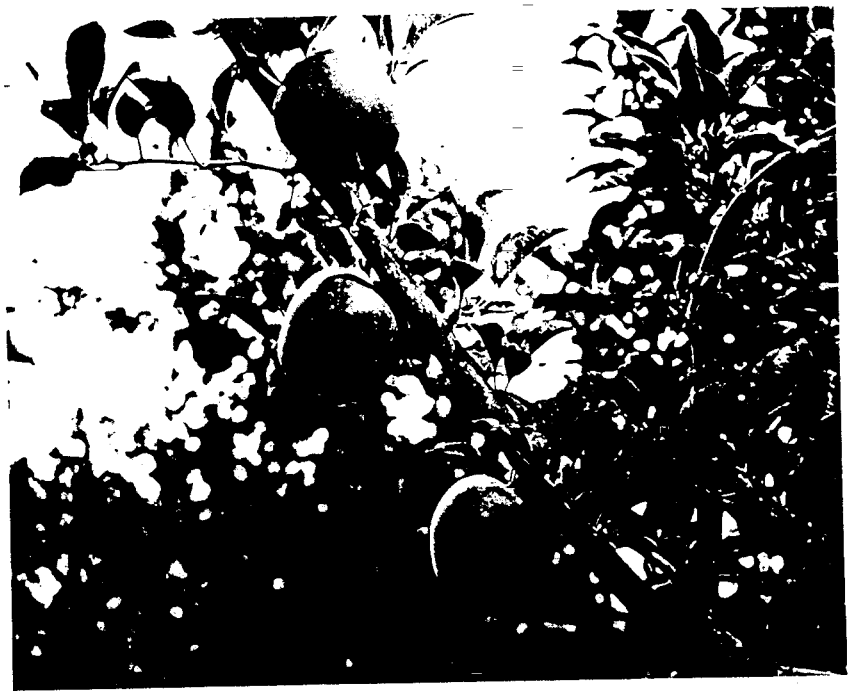

FIG. 12 is a photograph of a flower cluster of "Beni Tsugaru".

Figure 13:
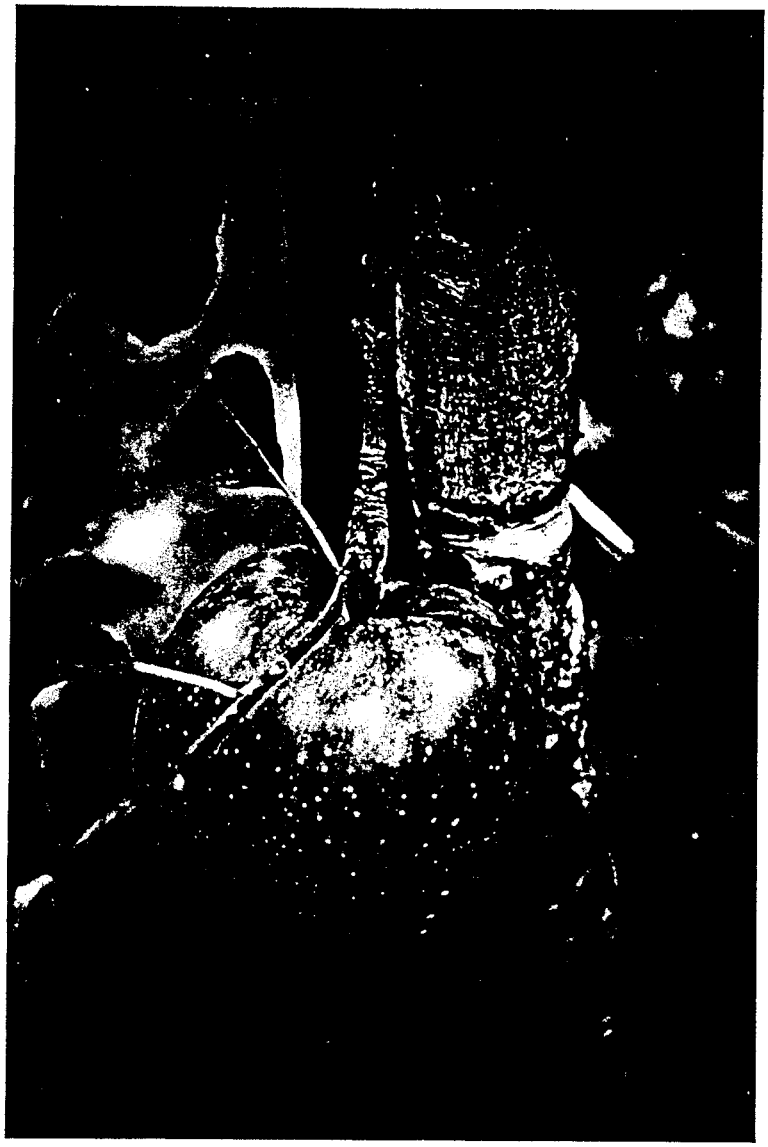

FIG. 13 is a photograph of unopened flowers of "Beni Tsugaru".

Figure 14:
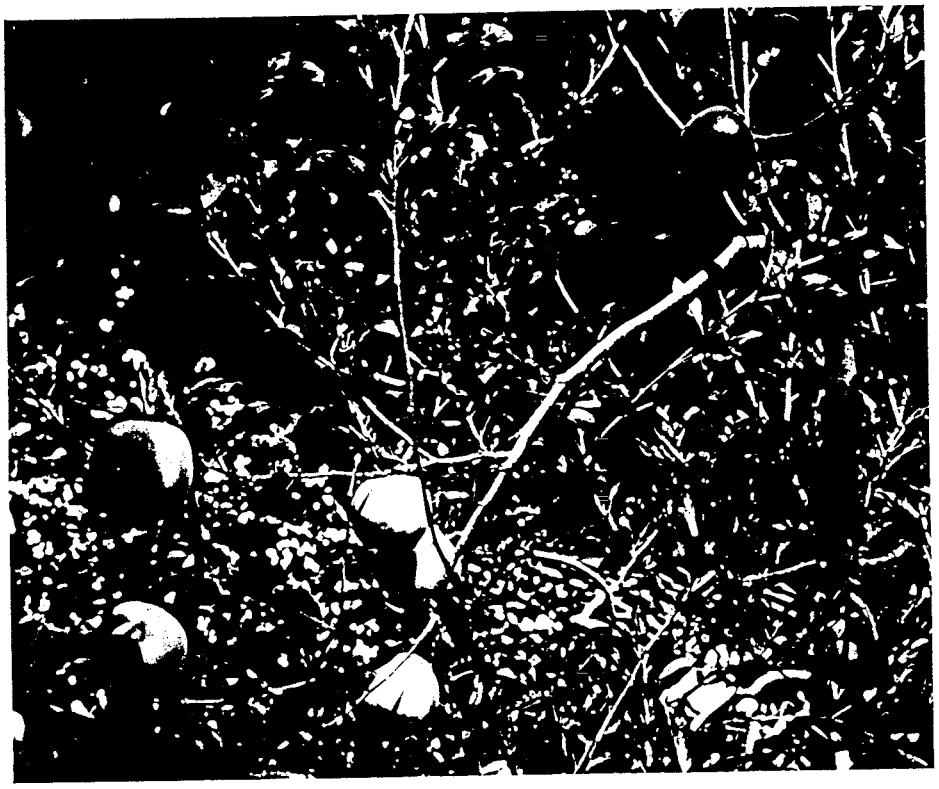

FIG. 14 is a photograph of flowers of "Beni Tsugaru".

Figure 15:
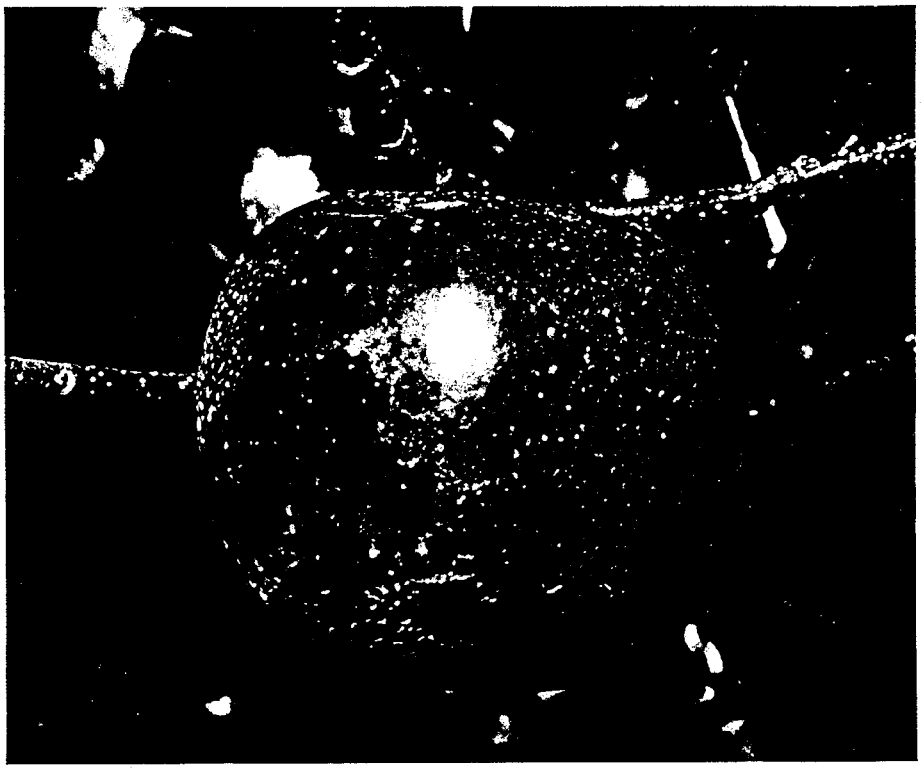

FIG. 15 is a photograph of leaves of "Beni Tsugaru".

Figure 16:
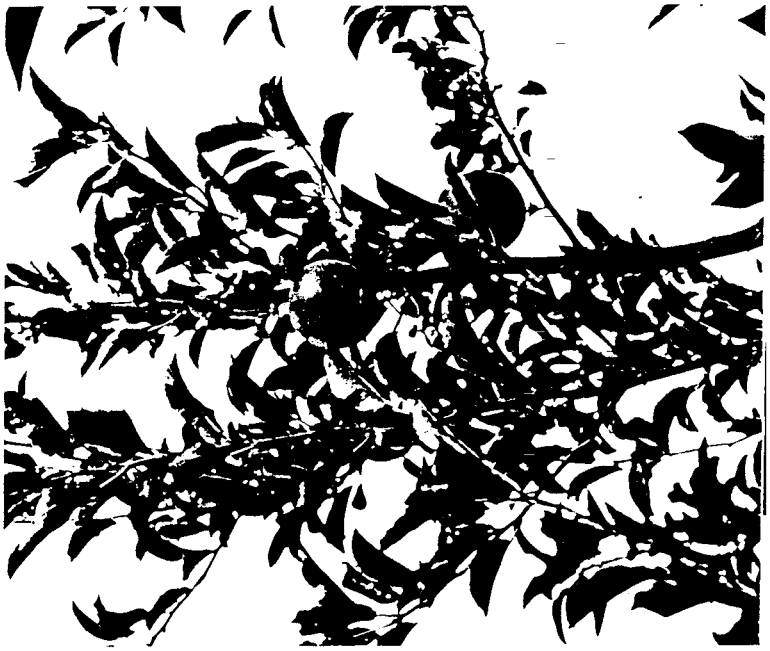

FIG. 16 is a photograph of "Beni Tsugaru" fruits on Starking Delicious tree.

Figure 17:
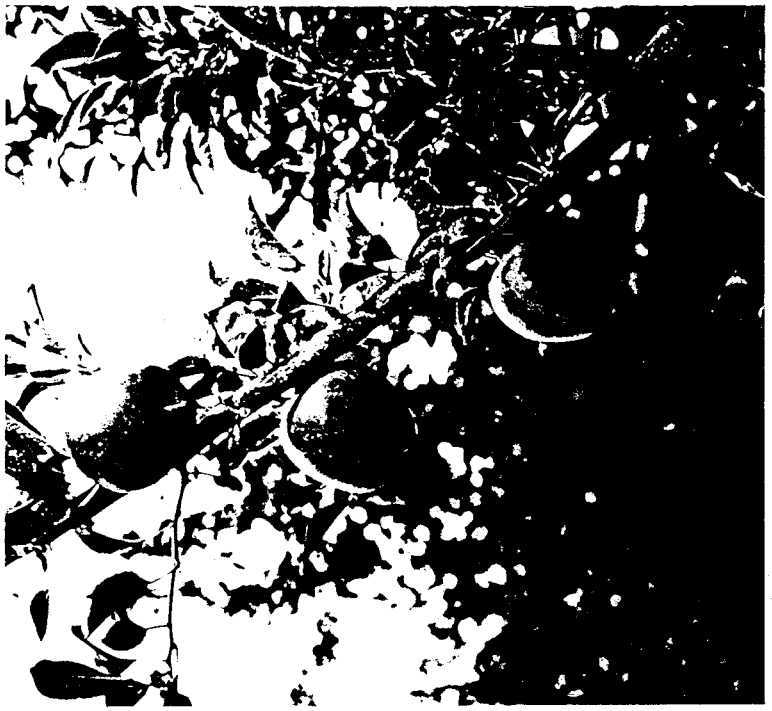

FIG. 17 is a photograph of "Beni Tsugaru" fruits on Starking Delicious tree.

Figure 18:
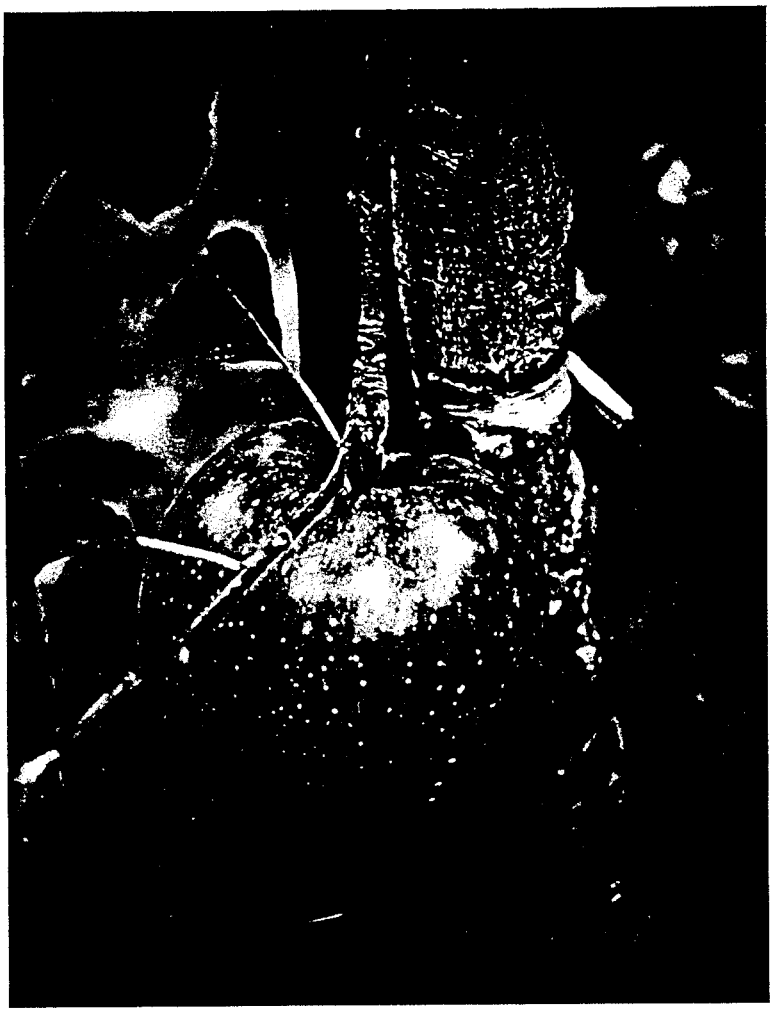

FIG. 18 is a photograph of "Beni Tsugaru" fruit on Jonagold tree.

Figure 19:
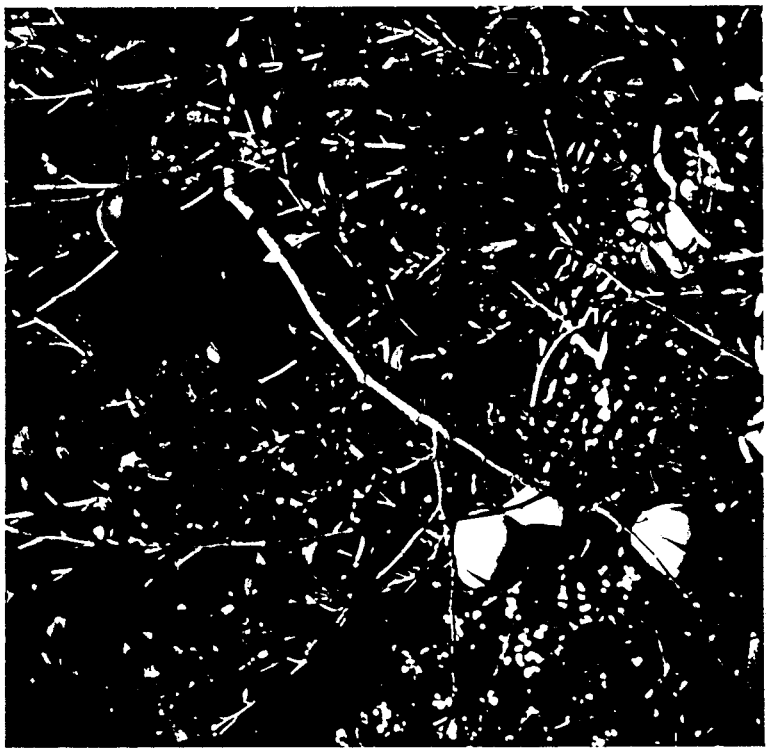

FIG. 19 is a photograph of "Beni Tsugaru" fruit compared with "Tsugaru" in orchard on Mr. T. Murakami. (The red fruit is "Beni Tsugaru", and the green fruit is "Tsugaru".)

Figure 20:
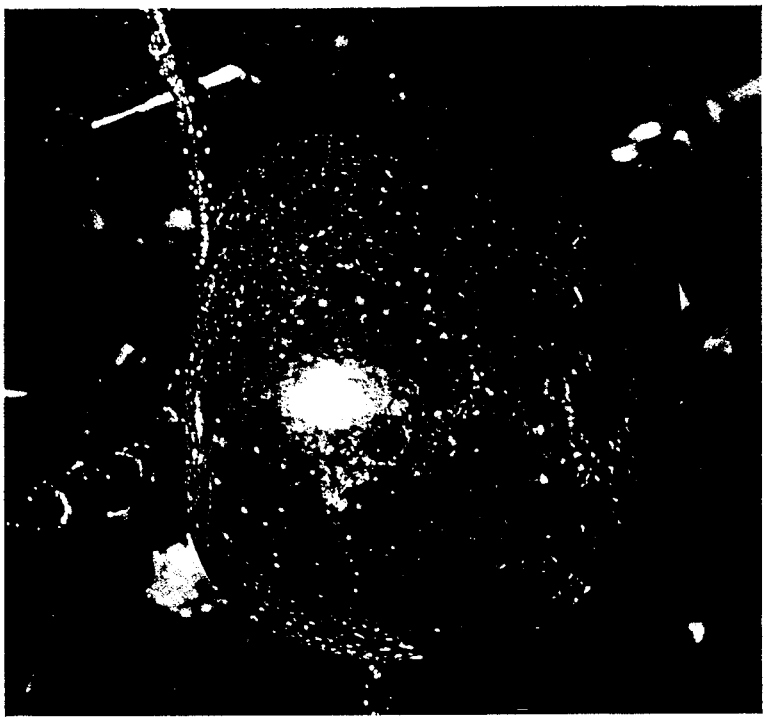

FIG. 20 is a photograph of "Beni Tsugaru" fruit on "Tsugaru" tree in Mr. T. Murakami's orchard.

DESCRIPTION OF THE INVENTION

The "Beni Tsugaru" apple was discovered by Kunihiko Ishizawa on a 10-year old "Tsugaru" limb top work on a 30-year old "Ralls Janet" apple tree in his orchard at Wada No. 256, Oodawara, Itayanagi cho, Kita tsugaru gun, Aomori prefecture, Japan, in late August, 1986. This fruit, which is the "Beni Tsugaru" apple variety of the invention, was already turning red at the time when the fruit of "Tsugaru" was still green. In early September, the fruit of "Beni Tsugaru" became overall solid red, in contrast to the "Tsugaru" fruit which had distinct stripes. Continued observation of the mutation over 3 years indicated that, as a stable characteristic, the fruit of "Beni Tsugaru" colors solid red about 20 days earlier than the "Tsugaru" fruit.

The inventor grafted budwoods of the invention onto Starking Delicious tree and a Jonagold tree on M26 tree in 1988. In 1990, he observed the first crop of fruits of the invention on Starking Delicious and Jonagold trees. It was observed that all of the fruits of the invention on Starking and Jonagold trees color overall solid red without stripes, the same as the mother tree. This confirms that progenies of the mutation color stably overall solid red, the same as the mother tree of the mutation. Further, Mr. Tsueno Murakami, an apple grower in the Aomori prefecture, tested the stability of the mutation in his orchards. He grafted the invention on "Tsugaru" trees in his orchard in 1988, and confirmed the stability of the coloring of the fruits of the mutation in 1990.

The following is a description of the characteristics of the apple variety of this invention.

Tree: Characterized by medium vigor, and spreading tendency.

Shoot: Chocolate color (Munsell 5YR 2/4), slender with many large lenticels and medium pubescence. The internode is approximately 2.53 cm on a one-year old tree. A one-year old shoot is dark reddish-brown (3YR 2.5/4) with many large round lenticels (much more than Fuji), with much pubescence. The bud is adpressed on a wavy shoot.

Leaf: Elongated with crenate serrations and waved margin. The margin of the leaf has more crenate serrations than "Tsugaru". Length of leaf blade is approximately 9.08 cm, width is approximately 5.32 cm, petiole is approximately 2.5 cm. Leaf color is green (Munsell 5GY 3/4). Stipule is falcate, with a length of approximately 1.19 cm.

Pollination: The tree of the present invention requires a pollinizer, such as "Red Gold", "Jonathan" or "Delicious", etc.

Flower: Small. Unopened flower is deep pink. The petal of the open flower turns white with ununiform pink to red stripes. Time of flowering is mid-season, same as for "Tsugaru".

Fruit:

*Shape.*—Oblong, without crowning, same as in "Tsugaru" and is of medium size (250–300 g). Ribs are indistinct. Aperture of eye is medium size. Basin and stalk cavity is of medium depth and breadth.

*Flesh.*—Creamy white, very juicy, moderately sweet (Brix 12.5), with low acidity. Flavor is light to insipid. Firmness and texture of fruit are medium. Browning is very unpronounced. Mature fruit has no water core.

Skin.—Ground color is yellowish green. Fruit skin is overall solid deep red, (Muncell 4R3/10) while "Tsugaru" fruit skin is covered with distinct stripes. The fruit skin of "Beni Tsugaru" has few medium size lenticels, and very slight russet around the stalk cavity. The skin is a little shiny, smooth, without bloom, and without cracking tendency.

*Core.*—Oval and medium size.

*Seed.*—Seed is large, obovate.

Harvest season: Early season, early September on original tree, about 20 days earlier than "Tsugaru". The skin of the fruit of "Beni Tsugaru" is 100% red (Muncell 4R3/10) in early September, whereas in the parent "Tsugaru" only 10–20% of the skin is colored red in early September. Fruit mature fully in late September. That is, fruit skin colors fully overall red in early September, but the flesh is slightly unripened at that time. In late September, the fruit of the invention tree is fully ripened and sweeter than "Tsugaru".

Storage life: Relatively long, in natural and cold storage. Fully matured fruits at late September can be stored in cold storage until late October. However, fully red colored, but slightly unripened fruits harvested at early September can be stored more than 10 days longer in cold storage. The fruits on the tree have a tendency to proceed quickly to mealy breakdown after proper ripening time.

Productivity: Tree is regularly productive and needs adequate fruit thinning.

Use: Good as dessert apple.

I claim:

1. A new and distinct variety of apple tree, substantially as illustrated and described herein, particularly characterized by fruit which colors solid red earlier than the known "Tsugaru" variety.

* * * * *